(12) United States Patent
Ikeda et al.

(10) Patent No.: US 7,893,404 B2
(45) Date of Patent: Feb. 22, 2011

(54) ELECTROMAGNETIC WAVE SENSOR, IMAGING ELEMENT AND IMAGING DEVICE

(75) Inventors: Naru Ikeda, Tokyo (JP); Hiroto Honda, Tokyo (JP); Yoshinori Iida, Tokyo (JP); Ikuo Fujiwara, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 554 days.

(21) Appl. No.: 11/856,255

(22) Filed: Sep. 17, 2007

(65) Prior Publication Data

US 2009/0015491 A1    Jan. 15, 2009

(30) Foreign Application Priority Data

Dec. 11, 2006    (JP) .............................. 2006-333226

(51) Int. Cl.
*G01J 5/20* (2006.01)
*G01J 5/02* (2006.01)

(52) U.S. Cl. ............................... 250/338.4; 250/339.01

(58) Field of Classification Search .............. 250/338.4, 250/339.02, 339.04, 370.01
See application file for complete search history.

(56) References Cited

U.S. PATENT DOCUMENTS

| 6,114,696 | A  | * | 9/2000  | Eden ........................ 250/338.1 |
| 6,329,655 | B1 |   | 12/2001 | Jack et al. |
| 6,441,368 | B1 |   | 8/2002  | Grinberg et al. |
| 6,985,116 | B2 |   | 1/2006  | Agnese et al. |
| 7,005,644 | B2 | * | 2/2006  | Ishikawa et al. ....... 250/339.04 |
| 2007/0260294 | A1 | * | 11/2007 | Schulman et al. ............. 607/60 |

FOREIGN PATENT DOCUMENTS

| JP | 08-320254   | 12/1996 |
| JP | 2006-086736 | 3/2006  |
| JP | 2006-121643 | 5/2006  |
| JP | 2006-170822 | 6/2006  |
| JP | 2006-300925 | 11/2006 |

OTHER PUBLICATIONS

Japanese Office Action dated Nov. 7, 2008 corresponding to U.S. Appl. No. 11/856,255, filed Sep. 17, 2007.

* cited by examiner

*Primary Examiner*—David P Porta
*Assistant Examiner*—Carolyn Igyarto
(74) *Attorney, Agent, or Firm*—Turocy & Watson, LLP

(57) ABSTRACT

The present invention enables to provide a simple and inexpensive electromagnetic wave sensor that selectively detects sub-millimeter waves and millimeter waves in a specific frequency band, an imaging element and an imaging device. The distance of the gap between a plurality of antenna elements is smaller than the wavelength of infrared light. A capacitor electrically formed by the gap between the plurality of antenna elements, and an electrical resistor portion form parallel circuits electrically coupled to the antenna portion. The plurality of antenna elements are formed so that the impedance of the antenna portion is matched with the impedance of the parallel circuits against electromagnetic waves having a predetermined frequency, and is not matched against the higher harmonics of electromagnetic waves having the predetermined frequency.

8 Claims, 3 Drawing Sheets

A-A SECTION

ELECTROMAGNETIC WAVE SENSOR, IMAGING ELEMENT AND IMAGING DEVICE

CROSS-REFERENCE TO RELATED APPLICATION

This application is based upon and claims the benefit of priority from prior Japanese Patent Application No. 2006-333226 filed on Dec. 11, 2006 in Japan, the entire contents of which are incorporated herein by reference.

BACKGROUND OF THE INVENTION

1. Field of the Invention

The present invention relates to an electromagnetic wave sensor that selectively detects a specific frequency band of electromagnetic waves, such as sub-millimeter waves and millimeter waves, an imaging element and an imaging device.

2. Related Art

Relative to infrared light having wavelengths of several micrometers to tens of micrometers, millimeter waves (wavelengths of several mm to 10 mm) and sub-millimeter waves (wavelengths of about 30 μm to 1 mm) having longer wavelengths, which is also referred to as terahertz light in recent years, have attracted attention as electromagnetic waves that provide new modes of sensing and imaging for their characteristics, such as high penetrative properties and noninvasiveness to substances as well as distinct spectral characteristics depending on materials or conditions, and have been technically matured by recent development in lasers or optoelectronics.

Means for detecting electromagnetic waves of this band include a method for indirectly detecting desired electromagnetic waves by combining an ultra-short pulse laser with nonlinear crystals or an optical switch; a method for electrically detecting electromagnetic waves using a semiconductor device, such as an ultrahigh-frequency diode; a method using a quantum detecting element, such as a superconductive element and quantum-dot element; and a method using a thermal detecting element, such as a bolometer and pyroelectric element.

Although the method using an ultra-short pulse laser is superior for spectroscopy because spectral information on the subject of measurement can be easily obtained, it requires the entire system including the laser, the optical system and the subject of measurement to be placed in a well-controlled atmosphere, and suffers from many limitations, such as requirement of equipment which is expensive as a whole, to find application in the industry.

Detection using an ultrahigh-frequency diode has been realized of only up to several hundred gigahertzes at present, and has technical difficulties for expansion to higher frequency side.

Although use of the quantum detecting element is an excellent method for detecting only electromagnetic waves of frequencies corresponding to specific inter-level transition, and is capable of high-speed detection at high-sensitivity, the thermal excitation of carriers must be suppressed and the element must be cooled to an extremely low temperature for detecting electromagnetic waves whose photon energy is extremely small, such as millimeter waves and sub-millimeter waves, at high-sensitivity. Therefore, the quantum detecting element requires a liquid coolant, such as liquefied helium, and the fabrication of a practical system is difficult.

The thermal detecting element detects temperature change resulted from heat generated by converting electromagnetic waves using certain means, as the change in the electrical characteristics of the element. Although the thermal detecting element is slower and less sensitive than the quantum detecting element, it has generally flat sensitivity characteristics over a broad band, and temperature environment for the sensor can advantageously be stabilized to simplify cooling requirement by introducing a heat-insulating structure or the like to support the element in the air. Therefore, the thermal detecting element has been put into practical use as an infrared image sensor in the infrared wavelength band, and as a radio telescope in the millimeter wave band. The detection wavelength band of the thermal detecting element is designed by optimizing the materials of the heating element to optically absorb electromagnetic waves, or by adding a structure that can be resonated at a specific wavelength, such as an antenna and a waveguide, to the heating element. In an example wherein a thermal detecting element is applied to an infrared image sensor, vanadium oxide, polysilicon, amorphous silicon, germanium, titanium or the like is used as the material for the heating element. A bolometer is disclosed, for example, in U.S. Pat. No. 6,441,368.

In the band of sub-millimeter waves or millimeter waves, which have longer wavelengths than infrared light, it is difficult to design the material that efficiently absorbs only electromagnetic waves having a specific frequency. Since the thermal detecting element detects change in the temperature of the heating element as signals accordingly, there is a problem wherein the thermal detecting element is easily affected by electromagnetic waves having wavelengths other than the wavelength in the frequency band to be detected.

At normal temperatures, naturally radiated light whose peak is infrared light in the 10 μm band is radiated from a subject of measurement and the surroundings, and the intensity of the sub-millimeter wave band is about one-thousandth lower than the infrared band. Therefore, an important technical challenge in the selective detection of millimeter waves or sub-millimeter waves using a thermal detecting element, whose wavelength selectivity is not fundamentally high, is to reduce the effect of infrared light contained in naturally radiated light. To detect millimeter waves or sub-millimeter waves, a thermal detecting element wherein, for example, a dipole antenna, whose size is a half the wavelength $\lambda$ to be detected, is joined to the heating element is available. There is a problem that, when naturally radiated light of a normal temperature is irradiated onto the thermal detecting element, the temperature of the heating element is elevated by direct irradiation or indirect irradiation by reflection from the surroundings or the like of infrared light, which is a major component of naturally radiated light. Since, with such an antenna, higher harmonics having wavelengths of an integral fraction of the wavelength $\lambda$ of electromagnetic waves is also detected in a certain efficiency in addition to electromagnetic waves having a wavelength of $\lambda$, and the higher harmonics of sub-millimeter waves fall within the infrared region, the infrared light, which is a major component of naturally radiated light, may pass through the antenna and heat the heating element, and it is difficult to selectively detect only a specific frequency band of millimeter waves or sub-millimeter waves at high sensitivity.

To reduce the effect of infrared light contained in the naturally radiated light, a method can be used wherein strong monochromatic light having millimeter waves or sub-millimeter waves is radiated to a substance, and the reflected, scattered or transmitted light is detected. However, in this band, only large-scale research equipment, such as a methanol laser and a free-electron laser, is at the present available as a high-output light source that can ignore the effect of naturally radiated light, and it is difficult to apply such a light source to practical systems. In another method, an optical filter that blocks infrared light but transmits millimeter waves and sub-millimeter waves is placed in front of the detecting element. For example, in the case of a radio telescope, the element itself is cooled to an extremely low temperature in addition to the wavelength selecting structure, such as an antenna and a wave guide, and an optical filter is used for blocking naturally radiated light from the exterior to detect imperceptible millimeter waves and sub-millimeter waves coming from space. However, such large-scale equipment configuration cannot provide a simple and inexpensive detecting device of millimeter waves and sub-millimeter waves.

SUMMARY OF THE INVENTION

To solve the above-described problems, an object of the present invention is to provide a simple and inexpensive electromagnetic wave sensor that can selectively detect millimeter waves or sub-millimeter waves having a specific frequency from natural radiant light at high-sensitivity, even when the natural radiant light is radiated from the exterior without cooling the element to an ultra-low temperature; and an imaging element and an imaging device using such electromagnetic wave sensors.

An electromagnetic wave sensor according to a first aspect of the present invention includes: a semiconductor substrate having a recess formed on the surface thereof;
a cell portion; and
a supporting portion having wiring portions electrically connected to the cell portion and supporting the cell portion in or on the recess,
the cell portion including:
an antenna portion having a plurality of antenna elements, for detecting incident electromagnetic waves and converting the electromagnetic waves into electrical signals;
an electrical resistor portion disposed below the antenna portion and electrically connected to each of the plurality of antenna elements, for converting electrical energy corresponding to the electrical signals into Joule heat to change the temperature of the cell portion; and
a thermoelectric conversion element electrically connected to the wiring portions, electrically insulated from the antenna portion and the electrical resistor portion, thermally connected to the electrical resistor portion, and for detecting the temperature change of the cell portion to convert the temperature change into electrical signals, and wherein
the distance of the gap between the plurality of antenna elements is smaller than the wavelength of infrared light.

An electromagnetic wave sensor according to a second aspect of the present invention includes: a semiconductor substrate having a recess formed on the surface thereof;
a cell portion; and
a supporting portion having wiring portions electrically connected to the cell portion and supporting the cell portion in or on the recess;
the cell portion including:
an antenna portion having a plurality of antenna elements, for detecting incident electromagnetic waves and converting the electromagnetic waves into electrical signals;
an electrical resistor portion disposed below the antenna portion and electrically connected to each of the plurality of antenna elements, for converting electrical energy corresponding to the electrical signals into Joule heat to change the temperature of the cell portion; and
a thermoelectric conversion element electrically connected to the wiring portions, electrically insulated from the antenna portion and the electrical resistor portion, thermally connected to the electrical resistor portion, and for detecting the temperature change of the cell portion to convert the temperature change into electrical signals, and wherein
a capacitor electrically formed by the gap between the plurality of antenna elements and the electrical resistor portion form a parallel circuit electrically coupled to the antenna portion, and the plurality of antenna elements are formed so that the impedance of the antenna portion and the impedance of the parallel circuit are matched for electromagnetic waves having a predetermined frequency, but the impedance is not matched for the higher harmonics of electromagnetic waves having the predetermined frequency.

An electromagnetic wave sensor according to a third aspect of the present invention includes: a semiconductor substrate having a recess formed on the surface thereof;
a cell portion; and
a supporting portion having wiring portions electrically connected to the cell portion and supporting the cell portion in or on the recess;
the cell portion including:
an antenna portion having a plurality of antenna elements, for detecting incident electromagnetic waves and converting the electromagnetic waves into electrical signals;
an electrical resistor portion disposed below the antenna portion and electrically connected to each of the plurality of antenna elements, for converting electrical energy corresponding to the electrical signals into Joule heat to change the temperature of the cell portion; and
a thermoelectric conversion element electrically connected to the wiring portions, electrically insulated from the antenna portion and the electrical resistor portion, thermally connected to the electrical resistor portion, and for detecting the temperature change of the cell portion to convert the temperature change into electrical signals, wherein
the distance of the gap between the plurality of antenna elements is smaller than the wavelength of infrared light; a capacitor electrically formed by the gap between the plurality of antenna elements and the electrical resistor portion form a parallel circuit electrically coupled to the antenna portion and the plurality of antenna elements are formed so that the impedance of the antenna portion and the impedance of the parallel circuit are matched for electromagnetic waves having a predetermined frequency, but the impedance is not matched for the higher harmonics of electromagnetic waves having the predetermined frequency.

An imaging element according to a fourth aspect of the present invention includes: a semiconductor substrate having a recess formed on the surface thereof;
a plurality of electromagnetic wave sensors disposed in a matrix arrangement as picture element arrays on the semiconductor substrate; and
a readout circuit for reading the electrical signals corresponding to electromagnetic waves detected by each of the electromagnetic wave sensors;
each of the electromagnetic wave sensor including:
a cell portion; and
a supporting portion having wiring portions electrically connected to the cell portion and supporting the cell portion in or on the recess,
the cell portion including:
an antenna portion having a plurality of antenna elements, for detecting incident electromagnetic waves and converting the electromagnetic waves into electrical signals,
an electrical resistor portion disposed below the antenna portion and electrically connected to each of the plurality of antenna elements, for converting electrical energy corresponding to the electrical signals into Joule heat to change the temperature of the cell portion, and a thermoelectric conversion element electrically connected to the wiring portion, electrically insulated from the antenna portion and the electrical resistor portion, thermally connected to the electrical resistor portion, and for detecting the temperature change of the cell portion to convert the temperature change into electrical signals; and wherein the distance of the gap between the plurality of antenna elements is smaller than the wavelength of infrared light.

An imaging device according to a fifth aspect of the present invention includes: an imaging element;

an evacuated package wherein the imaging element is encapsulated;

an optical window disposed in the electromagnetic-wave incidence plane of the package, and transmitting electromagnetic waves of a specific frequency of incident electromagnetic waves;

an optical element for focusing and imaging incident electromagnetic waves on the imaging element in the package through the optical window; and a picture signal processing section connected to the imaging element and processing picture signals outputted from the imaging element, the imaging element comprising:

a semiconductor substrate having a recess formed on the surface thereof;

a plurality of electromagnetic wave sensors disposed in a matrix arrangement as picture element arrays on the semiconductor substrate; and a readout circuit for reading the electrical signals corresponding to electromagnetic waves detected by each of the electromagnetic wave sensors as image signals, each of the electromagnetic wave sensors comprising:

a cell portion; and a supporting portion having wirings electrically connected to the cell portion and supporting the cell portion in or on the recess, the cell portion comprising:

an antenna portion having a plurality of antenna elements, for detecting incident electromagnetic waves and converting the electromagnetic waves into electrical signals;

an electrical resistor portion disposed below the antenna portion and electrically connected to each of the plurality of antenna elements composing the antenna portion, for converting electrical energy corresponding to the electrical signals into Joule heat to change the temperature of the cell portion; and a thermoelectric conversion element electrically connected to the wiring portion, electrically insulated from the antenna portion and the electrical resistor portion, thermally connected to the electrical resistor portion, and for detecting the temperature change of the cell portion to convert the temperature change into electrical signals; and wherein the distance of the gap between the plurality of antenna elements is smaller than the wavelength of infrared light.

DETAILED DESCRIPTION OF THE INVENTION

Figure 1:
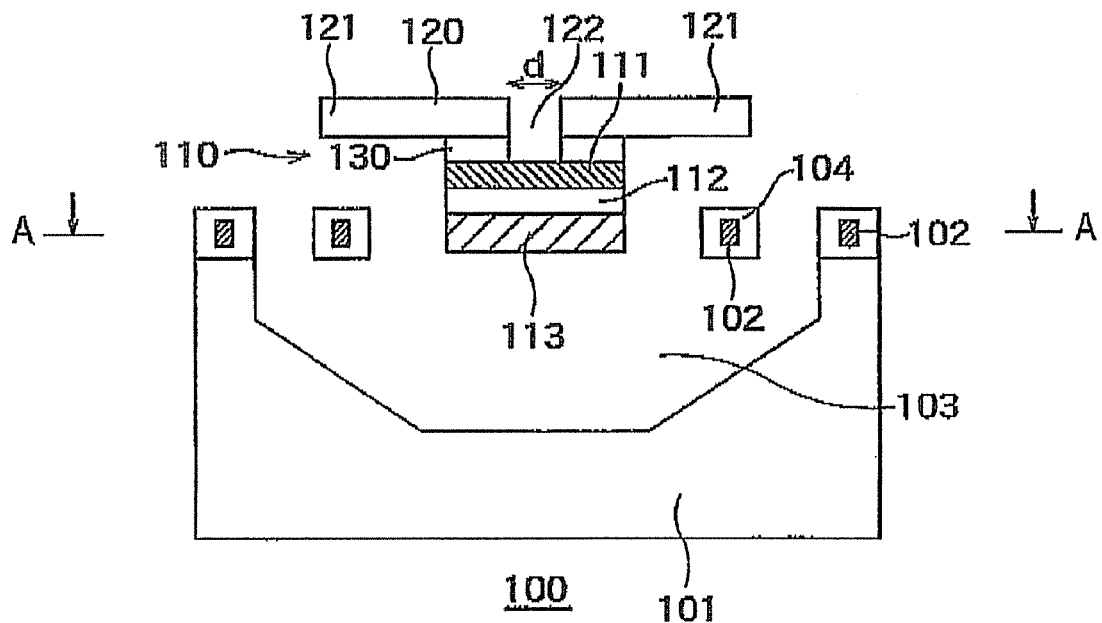
FIG. 1 is a sectional view showing an electromagnetic wave sensor according to an embodiment of the present invention.

An electromagnetic wave sensor, an imaging element and an imaging device according to an embodiment of the present invention will be described in detail referring to the drawings.

(Structure of Electromagnetic Sensor)

Figure 5:
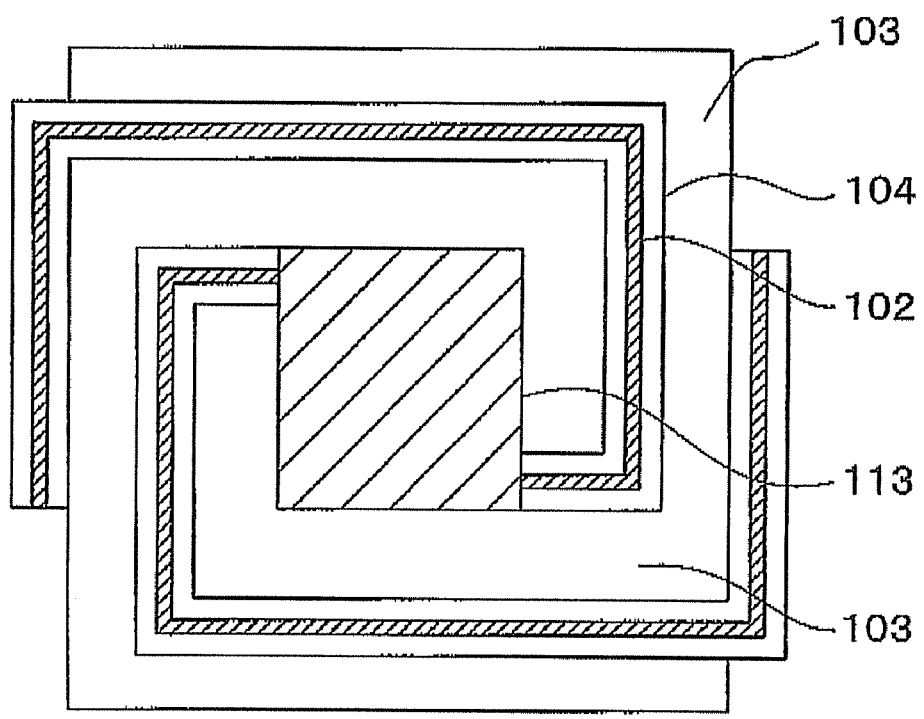
FIG. 5 is a plan view showing the electromagnetic wave sensor of FIG. 1.

FIG. 1 and FIG. 5 show the configuration of an electromagnetic wave sensor 100 according to an embodiment of the present invention. The electromagnetic wave sensor 100 has a semiconductor substrate 101; wiring portions 102 formed on the semiconductor substrate 101; a recess 103 formed in the surface area of the semiconductor substrate 101; supporting portions 104 for supporting the wiring portions 102, disposed in the recess 103 or on the recess 103; and a cell unit 110 disposed in the recess 103 or on the recess 103, and supported by the supporting portions 104.

The cell unit 110 has an antenna portion 120, an electrical resistor portion 111 and a thermoelectric conversion element 113. The antenna portion 120 is formed of a plurality of antenna elements 121, detects incident electromagnetic waves and converts the electromagnetic waves into electric signals. The electrical resistor portion 111 is disposed below the antenna portion 120, electrically connected to each of the plurality of antenna elements 121 forming the antenna portion 120, and changes the temperature of the cell unit 110 by converting the electrical energy corresponding to the electric signals into Joule heat. The thermoelectric conversion element 113 is electrically connected to the wiring portions 102, electrically insulated from the antenna portion 120 and the electrical resistor portion 111, and thermally connected to the electrical resistor portion 111. The thermoelectric conversion element 113 continuously detects temperature change of the cell unit 110, and converts the temperature change into electric signals. To realize the above-described structure, for example as shown in FIG. 1, an antenna contact 123 can be provided between the antenna portion 120 and the electrical resistor portion 111, or an insulating film 112 can be provided between the thermoelectric conversion element 113 and the electrical resistor portion 111.

Furthermore, in the case of the embodiment, the distance d of a gap 122 between the plurality of antenna elements 121 is designed to be smaller than the wavelength of infrared light.

A capacitor electrically formed by the gap 122 between the plurality of antenna elements 121, and the electrical resistor portion 111 form parallel circuits electrically connected to the antenna portion 120. The plurality of antenna elements 121 are formed so that the impedance of the antenna portion 120 is matched with the impedance of the parallel circuits for electromagnetic waves having a predetermined frequency, and is not matched for the higher harmonics of electromagnetic waves having the predetermined frequency.

As a material of the antenna portion 120, it is desirable to use a metal that has high electric conductivity and highly reflects infrared light, such as aluminum and copper. As the electrical resistor portion 111, a semiconductor, a metal oxide or the like can be used, and it is desirable to use a material suitable for the manufacturing process and that has an adequate electric resistivity considering impedance matching with the antenna portion 120. Furthermore, as the thermoelectric conversion element 113, it is desirable to use an element whose electrical properties change by change in temperature, such as a bolometer, a pyroelectric element, a thermopile element and a diode. In this case, the distance of the gap between the plurality of antenna elements should be smaller than the wavelength of infrared light. It is also desirable to design the plurality of antenna elements for the impedance matching described above.

(Operation of Sensor)

Next, the operation when electromagnetic waves, such as natural radiation, are incident in the electromagnetic wave sensor 100 is described. In the electromagnetic wave sensor 100, the electrical resistor portion 111 is disposed below the antenna elements 121, and by forming a metal having a sufficient thickness (e.g., at least 200 nm) as the antenna portion 120, most of incident infrared light is reflected by the antenna elements 121.

Even if a part of the electrical resistor portion 111 is exposed in the gap 122 between the antenna elements 121, since the distance d of the gap 122 is designed to be sufficiently smaller (e.g., 0.5 µm) than the wavelength of infrared light, (e.g., wavelengths of 50 µm to 3 µm), which is the major component of natural radiation, the generation of heat in the electrical resistor 111 by the irradiation of the infrared light through the gap 122 can be negligibly reduced.

On the other hand, the antenna portion 120 of the electromagnetic wave sensor 100 can be an antenna having a length of a half the wavelength $\lambda$ of millimeter waves or sub-millimeter waves to be detected, such as a dipole antenna. The characteristic impedance Za of the antenna portion 120 can be represented using the inductance of the antenna portion 120 and the capacitance between the antenna portion 120 and the substrate and the like within an ultrahigh frequency bands, such as millimeter waves and sub-millimeter waves, and Za can be designed so as to match the impedance of vacuum for electromagnetic waves, such as Za=100Ω.

Whereas, since the length of the gap 122 between the antenna elements 121 is sufficiently smaller than the design wavelength $\lambda$ and the wavelength of infrared light, the parallel circuit composed of a capacitor formed by the gap 122 and the electrical resistor 111 can be handled as a lumped-parameter circuit, and the impedance Zg thereof can be represented using the resistance value R of the electrical resistor 111, the capacitance Cg of the capacitor formed by the gap 122, and the angle frequency ω as:

$$Zg=R/(1+j\omega CgR).$$

For example, when R is 100Ω, the distance d of the gap 122 is 0.5 µm, the area S of the antenna element 121 is 2×2 µm², and the gap 122 is in vacuum, $Cg=\epsilon_0 \cdot S/d = 7 \times 10^{-17}$ F where $\epsilon_0$ is a dielectric constant in vacuum. When the antenna contact 123 is formed under the antenna elements 121 as shown in FIG. 1, the area of the antenna contact 123 facing the gap 122 must be included in the area S of the antenna elements 121.

Figure 2:
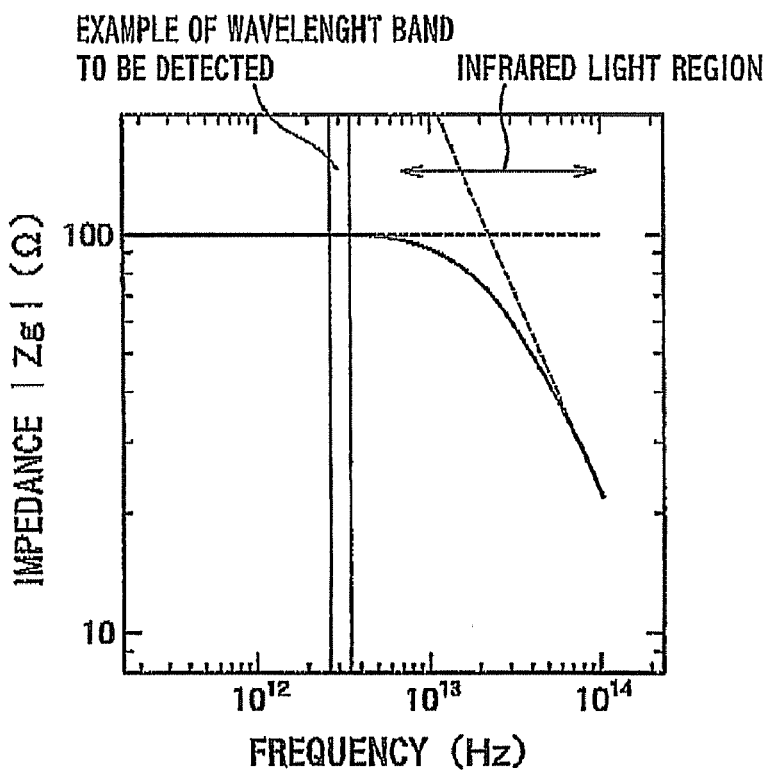
FIG. 2 is a graph of change in impedance of parallel circuits for illustrating the operation of an electromagnetic wave sensor according to an embodiment of the present invention.

In this case, as shown in FIG. 2, it is found that although the size of Zg is substantially consistent with Za in the longer wavelength side than about 100 µm (lower frequency side), Zg becomes smaller than Za in the shorter wavelength side (higher frequency side). Therefore, for example, when the wavelength $\lambda$ of sub-millimeter waves to be detected by the electromagnetic wave sensor 100 is 100 µm (frequency: 3 THz), and the length of the dipole antenna is 50 µm, which is ½ wavelength, the impedance of the electromagnetic wave sensor 100 is matched with the impedance of the antenna portion 120 and the parallel circuit for the electromagnetic waves of the wavelength of 100 µm, and efficient detection can be expected.

On the other hand, it is found that most of 50 µam (6 THz), 33 µm (9 THz), 25 µm (12 THz), and so forth, which are harmonics at $\lambda$=100 µm are reflected because the impedance Zg of the parallel circuit does not match the impedance Za of the antenna portion 120 even if received by the antenna portion 120, and the ratio of conversion to heat in the electrical resistor portion 111 is extremely lowered. This effect is larger as the wavelength of higher harmonics is shorter.

On the other hand, electromagnetic waves of the longer wavelength side than the wavelength $\lambda$ of the electromagnetic waves to be detected do not resonate with the antenna portion 120 because the half wavelength is larger than the length of the antenna portion 120. Therefore, the effect of the electromagnetic waves in the long-wavelength side to the electromagnetic wave sensor 100 according to the embodiment can be ignored.

According to the present embodiment, as described above, the generation of heat in the electrical resistor 111 by the irradiation of the infrared light, which is a major component of natural radiation, through the gap 122 between a plurality of antenna elements 121 can be negligibly reduced. Furthermore, since the impedance of the parallel circuit does not match the impedance of the antenna portion 120 in the shorter wavelength side than the wavelength $\lambda$ to be detected (high-frequency side), most of infrared light is reflected, and the generation of heat converted on the electrical resistor portion 111 can be extremely reduced. By the synergic action of these two effects, the selective detection of the electromagnetic waves in a predetermined wavelength band at high sensitivity can be realized.

Figure 6:
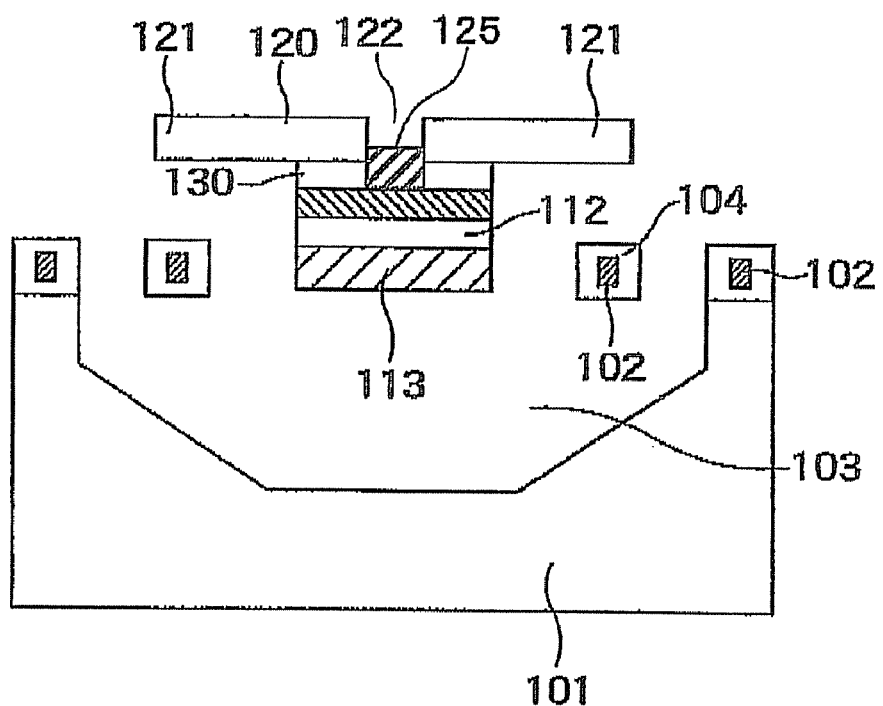
FIG. 6 is a sectional view showing the electromagnetic wave sensor according to a modification of the embodiment.

The length of the gap 122 between the antenna elements 121 is within a range between 0.1 µm and 10 µm. A part of or the entire gap 122 between the antenna elements 121 can be filled with a dielectric material. Although it is desired that the gap 122 between the antenna elements 121 is substantially in vacuum or filled with air or the like, the capacitance of the capacitor electrically formed by the gap 122 can be adequately designed by filling a part of or the entire gap 122 with insulator materials or dielectric materials 125 (see FIG. 6), and the impedance of the parallel circuit formed by the capacitor and the electrical resistor 111 can be matched with the impedance of the antenna portion 120. At this time, by disposing the dielectric material below the gap 122, the dielectric material can be made not to absorb infrared light.

Through the above-described actions, the effect of natural radiation can be reduced, and the selective detection of only the electromagnetic waves in a predetermined wavelength band at high sensitivity can be realized by using the electromagnetic wave sensor 100 according to the present embodiment. Although a dipole antenna is used for the antenna portion 120 as an example for description, the effect of the present embodiment is not limited thereto, but is effective to antennas having other structures, such as a bow-tie antenna and a log periodic antenna.

To detect electromagnetic waves having specific polarization, the antenna pattern can be designed to satisfy the object by using, for example, a dipole antenna wherein two antenna elements facing each other across the gap, whereas, to elevate the detecting sensitivity without a specified polarization, by using a crucial dipole antenna or a bow-tie antenna.

(Method for Manufacturing Electromagnetic Wave Sensor 100)

The electromagnetic wave sensor 100 according to the present embodiment can be manufactured by, for example, the following method: First, a SOI (silicon on insulator) substrate is prepared, and a thermoelectric conversion element 113 is formed on the SOI layer of the SOI substrate. On the layers above the SOI layer, a wiring portion and an insulating film 112 are formed. Next, the insulating film 112 is patterned and an etching hole is formed by RIE (reaction ion etching) to form a protective film for the support portion.

Next, to form an antenna, a sacrifice layer is formed on the SOI substrate so as to bury the etching hole. A contact hole is formed by etching the sacrifice layer to expose the surface of the insulating film 112 disposed on the thermoelectric conversion element 113, and an electrical resistor portion 111 is formed on the insulating film 112 in the contact hole and patterning is performed.

Next, on the sacrifice layer, the insulating film 112 and the electrical resistor portion 111, a lower antenna protective film, antenna contacts 123, a metal film to be an antenna portion 120, and an upper antenna protective film are sequentially formed. It is desired to use a low-resistance metal, such as Al, for the antenna portion 120. The shape of the antenna portion 120 and the gap 122 between antenna elements 121 are formed by patterning the upper antenna protective film, the metal film, and the lower antenna protective film by RIE, and the surface of the sacrifice layer is exposed by this process.

Thereafter, by etching the sacrifice layer and the semiconductor substrate 101 to remove a part of the semiconductor substrate 101, a recess 103 is formed below a cell portion 110 composed of the thermoelectric conversion element 113, the interlayer insulating film 112, the electrical resistor portion 111 and the like. Next, the upper antenna protective film is etched off to expose the antenna portion 120. The lower antenna protective film may be removed or may be left. By the above-described process, the electromagnetic wave sensor 100 of the present embodiment can be formed.

(Structure of Imaging Element)

Figure 3:
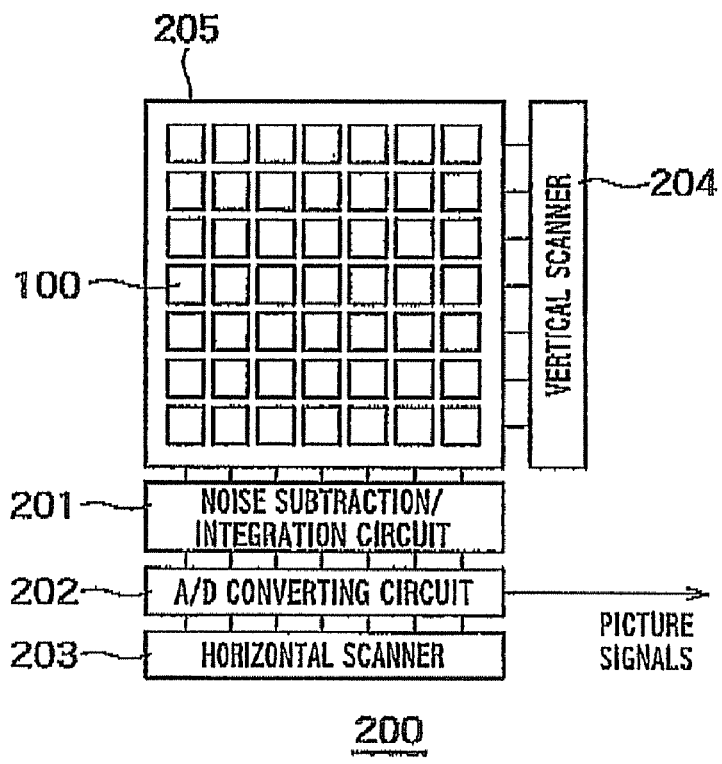
FIG. 3 is a schematic diagram showing an imaging element according to an embodiment of the present invention.

FIG. 3 shows the configuration of an imaging element 200 formed in a matrix arrangement of the above-described electromagnetic wave sensors 100. In the imaging element 200, electromagnetic wave sensors 100 are arrayed on a semiconductor substrate in a matrix, and signals detected by each electromagnetic wave sensor 100 are sequentially outputted by a readout circuit as picture signals.

Specifically, as shown in FIG. 3, the imaging element 200 is composed of a picture element array 205 formed by arraying such electromagnetic wave sensors 100 in a matrix, and a readout circuit. The readout circuit is composed of a vertical scanner 204 that sequentially supplies bias voltage to each line of the picture element array 205, a Noise subtraction/integration circuit 201 for processing the output signals from the electromagnetic wave sensors 100 positioned in a selected row in parallel, an A/D converting circuit 202, and a horizontal scanner 203 that serially outputs the signals read in parallel.

(Structure of Imaging Device)

Figure 4:
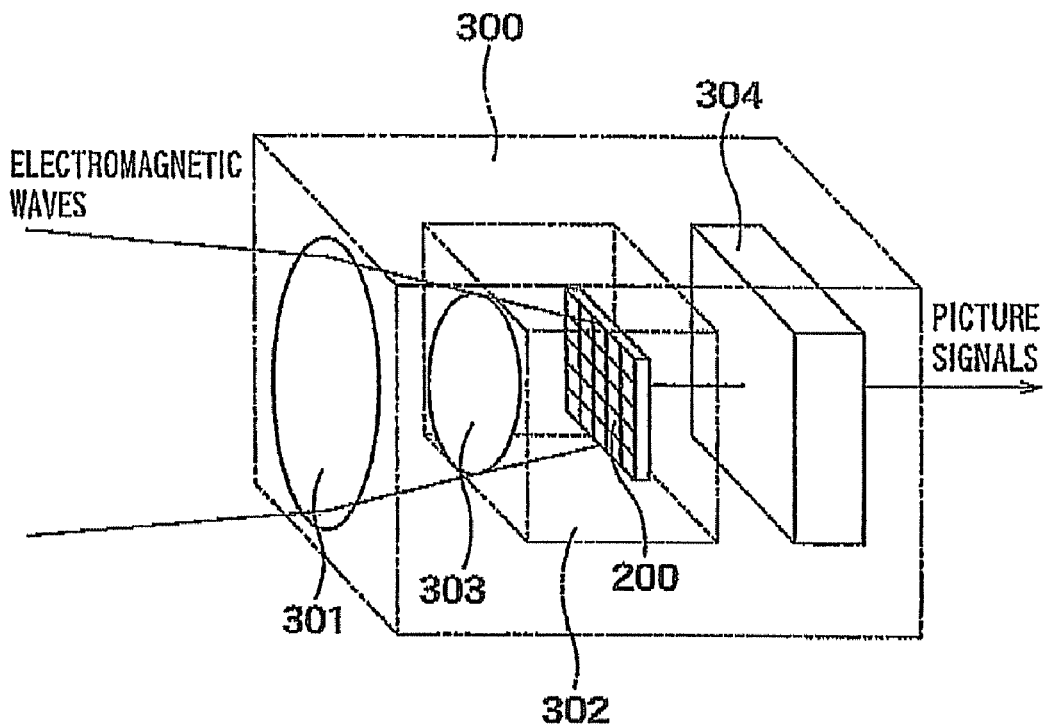
FIG. 4 is a schematic perspective view showing an imaging device according to an embodiment of the present invention.

FIG. 4 shows the configuration of an imaging device 300 having the above-described imaging element 200. The imaging device 300 is formed by encapsulating the imaging element 200 in a package 302. The package 302 is evacuated, and an optical window 303 that transmits electromagnetic waves having a specific frequency is disposed on the side of the package 302 facing the imaging element 200. The incident electromagnetic waves having the specific frequency are condensed and imaged by an optical element 301 through the optical window 303 onto the imaging element 200 in a package 302. The imaging element 200 is connected to a picture signal processing section 304, and the electric signals in the imaging element 200 are processed by the picture signal processing section 304.

The material of the optical window 303 composing the imaging device 300 according to the present embodiment is preferably a material that substantially transmits millimeter waves and sub-millimeter waves to be detected. Specifically, the examples of the usable materials include inorganic materials, such as silicon, germanium, quartz, and sapphire glass; and organic materials, such as polyethylene, polystyrene, polycarbonate, and Teflon (trademark). As the optical element 301, a lens or concave mirror that condenses electromagnetic waves can be used; and as the material for the lens, a material equivalent to the material for the optical window 303 can be used.

According to each embodiment of the present invention, even when natural radiant light is incident from the exterior, the effect of infrared light, which is a major component of natural radiant light, can be maintained small, and millimeter waves and sub-millimeter waves having a specific frequency can be selectively detected at high sensitivity.

The present invention is not limited to the above-described embodiments as they are, but in the stages of implementation, the present invention can also be embodied by modifying the constituents without departing from the scope thereof. Various inventions can be devised by adequately combining a plurality of constituents disclosed in the embodiments. For example, some constituents described in the embodiments may be deleted. Furthermore, constituents in different embodiments may be optionally combined.

What is claimed is:

1. An electromagnetic wave sensor comprising:
a semiconductor substrate having a recess formed on a surface thereof;
a cell portion; and
a supporting portion having wiring portions electrically connected to the cell portion and supporting the cell portion in or on the recess;
the cell portion comprising:
an antenna portion having a plurality of antenna elements, for detecting incident electromagnetic waves and converting the electromagnetic waves into electrical signals;
an electrical resistor portion disposed below the antenna portion and electrically connected to each of the plurality of antenna elements, for converting electrical energy corresponding to the electrical signals into Joule heat to change the temperature of the cell portion; and
a thermoelectric conversion element electrically connected to the wiring portions, electrically insulated from the antenna portion and the electrical resistor portion, thermally connected to the electrical resistor portion, and for detecting the temperature change of the cell portion to convert the temperature change into electrical signals, and wherein
a capacitor electrically formed by a gap between the plurality of antenna elements and the electrical resistor portion form a parallel circuit electrically coupled to the antenna portion, and the plurality of antenna elements are formed so that the impedance of the antenna portion and the impedance of the parallel circuit are matched for electromagnetic waves having a predetermined frequency, but the impedance is not matched for higher harmonics of electromagnetic waves having the predetermined frequency.

2. The sensor according to claim 1, wherein the gap between the antenna elements is within a range between 0.1 μm and 10 μm.

3. The sensor according to claim 1, wherein a part of or the entire gap between the antenna elements is filled with a dielectric material.

4. An electromagnetic wave sensor comprising:
a semiconductor substrate having a recess formed on a surface thereof;
a cell portion; and
a supporting portion having wiring portions electrically connected to the cell portion and supporting the cell portion in or on the recess;
the cell portion comprising:
an antenna portion having a plurality of antenna elements, for detecting incident electromagnetic waves and converting the electromagnetic waves into electrical signals;
an electrical resistor portion disposed below the antenna portion and electrically connected to each of the plurality of antenna elements, for converting electrical energy corresponding to the electrical signals into Joule heat to change the temperature of the cell portion; and
a thermoelectric conversion element electrically connected to the wiring portions, electrically insulated from the antenna portion and the electrical resistor portion, thermally connected to the electrical resistor portion, and for detecting the temperature change of the cell portion to convert the temperature change into electrical signals, wherein
the distance of a gap between the plurality of antenna elements is smaller than the wavelength of infrared light;
a capacitor electrically formed by the gap between the plurality of antenna elements and the electrical resistor portion form a parallel circuit electrically coupled to the antenna portion and the plurality of antenna elements are formed so that the impedance of the antenna portion and the impedance of the parallel circuit are matched for electromagnetic waves having a predetermined frequency, but the impedance is not matched for higher harmonics of electromagnetic waves having the predetermined frequency.

5. The sensor according to claim 4, wherein the gap between the antenna elements is within a range between 0.1 μm and 10 μm.

6. The sensor according to claim 4, wherein a part of or the entire gap between the antenna elements is filled with a dielectric material.

7. An imaging element comprising:
a semiconductor substrate having a recess formed on a surface thereof;
a plurality of electromagnetic wave sensors disposed in a matrix arrangement as picture element arrays on the semiconductor substrate, and each of the electromagnetic wave sensors sensing millimeter waves or sub-millimeter waves; and
a readout circuit for reading the electrical signals corresponding to electromagnetic waves detected by each of the electromagnetic wave sensors;
each of the electromagnetic wave sensor comprising:
a cell portion; and
a supporting portion having wiring portions electrically connected to the cell portion and supporting the cell portion in or on the recess,
the cell portion comprising:
an antenna portion having a plurality of antenna elements, for detecting incident electromagnetic waves and converting the electromagnetic waves into electrical signals,
an electrical resistor portion disposed below the antenna portion and electrically connected to each of the plurality of antenna elements, for converting electrical energy corresponding to the electrical signals into Joule heat to change the temperature of the cell portion, and
a thermoelectric conversion element electrically connected to the wiring portion, electrically insulated from the antenna portion and the electrical resistor portion, thermally connected to the electrical resistor portion, and for detecting the temperature change of the cell portion to convert the temperature change into electrical signals;
wherein the distance of a gap between the plurality of antenna elements is smaller than the wavelength of infrared light, and
wherein a capacitor electrically formed by the gap between the plurality of antenna elements and the electrical resistor portion form a parallel circuit electrically coupled to the antenna portion, and the plurality of antenna elements are formed so that the impedance of the antenna portion and the impedance of the parallel circuit are matched for electromagnetic waves having a predetermined frequency, but the impedance is not matched for higher harmonics of electromagnetic waves having the predetermined frequency.

8. An imaging device comprising:
an imaging element;
an evacuated package wherein the imaging element is encapsulated;
an optical window disposed in the electromagnetic-wave incidence plane of the package, and transmitting electromagnetic waves of a specific frequency of incident electromagnetic waves;
an optical element for focusing and imaging incident electromagnetic waves on the imaging element in the package through the optical window; and
a picture signal processing section connected to the imaging element and processing picture signals outputted from the imaging element,
the imaging element comprising:
a semiconductor substrate having a recess formed on a surface thereof;
a plurality of electromagnetic wave sensors disposed in a matrix arrangement as picture element arrays on the semiconductor substrate, and each of the electromagnetic wave sensors sensing millimeter waves or sub-millimeter waves; and
a readout circuit for reading the electrical signals corresponding to electromagnetic waves detected by each of the electromagnetic wave sensors as image signals,
each of the electromagnetic wave sensors comprising:
a cell portion; and
a supporting portion having wirings electrically connected to the cell portion and supporting the cell portion in or on the recess,
the cell portion comprising:
an antenna portion having a plurality of antenna elements, for detecting incident electromagnetic waves and converting the electromagnetic waves into electrical signals;
an electrical resistor portion disposed below the antenna portion and electrically connected to each of the plurality of antenna elements composing the antenna portion, for converting electrical energy corresponding to the electrical signals into Joule heat to change the temperature of the cell portion; and a thermoelectric conversion element electrically connected to the wiring portion, electrically insulated from the antenna portion and the electrical resistor portion, thermally connected to the electrical resistor portion, and for detecting the temperature change of the cell portion to convert the temperature change into electrical signals;

wherein the distance of a gap between the plurality of antenna elements is smaller than the wavelength of infrared light, and wherein a capacitor electrically formed by the gap between the plurality of antenna elements and the electrical resistor portion form a parallel circuit electrically coupled to the antenna portion, and the plurality of antenna elements are formed so that the impedance of the antenna portion and the impedance of the parallel circuit are matched for electromagnetic waves having a predetermined frequency, but the impedance is not matched for higher harmonics of electromagnetic waves having the predetermined frequency.

* * * * *